(12) United States Patent
Arcos et al.

(10) Patent No.: US 12,137,892 B2
(45) Date of Patent: Nov. 12, 2024

(54) INSERTION INSTRUMENTS (71) Applicant: AXIS SPINE TECHNOLOGIES LTD, St. Albans (GB)

(72) Inventors: Jonathan Arcos, St. Albans (GB); Christopher Reah, St. Albans (GB); Charles Barfield, Hernando, MS (US); Michael Sherman, Memphis, TN (US)

(73) Assignee: AXIS SPINE TECHNOLOGIES LTD, Reading (GB)

( * ) Notice: Subject to any disclaimer, the term of this patent is extended or adjusted under 35 U.S.C. 154(b) by 243 days.

(21) Appl. No.: 17/629,349

(22) PCT Filed: Jul. 24, 2020

(86) PCT No.: PCT/GB2020/051789
§ 371 (c)(1),
(2) Date: Jan. 21, 2022

(87) PCT Pub. No.: WO2021/014173
PCT Pub. Date: Jan. 28, 2021

(65) Prior Publication Data
US 2022/0249081 A1 Aug. 11, 2022

(30) Foreign Application Priority Data

Jul. 25, 2019 (GB) ..................... 1910640

(51) Int. Cl.
*A61B 17/02* (2006.01)
*A61F 2/46* (2006.01)
*A61F 2/30* (2006.01)

(52) U.S. Cl.
CPC .......... *A61B 17/025* (2013.01); *A61F 2/4611* (2013.01); *A61B 2017/0256* (2013.01);
(Continued)

(58) Field of Classification Search
CPC ......... A61B 17/02; A61B 17/025; A61F 2/46; A61F 2/4611
See application file for complete search history.

(56) References Cited

U.S. PATENT DOCUMENTS 6,045,579 A 4/2000 Hochshuler et al.
6,102,950 A 8/2000 Vaccaro
(Continued)

FOREIGN PATENT DOCUMENTS

CA 2381734 A 3/2001
DE 102012023042 11/2013
(Continued)

OTHER PUBLICATIONS

Product Brochure "InFix Anterior Lumbar Device—Surgical Technique Guide", Zimmer Biomet, 2018, pp. 1-28. Copyright 2018.
(Continued)

*Primary Examiner* — Christopher J Beccia
(74) *Attorney, Agent, or Firm* — LIU & LIU (57) ABSTRACT

The insertion instrument (10) for inserting a modular intervertebral fusion device or components thereof into an inter-vertebral space comprises at least one superior (arm 16), (18) mounted on a superior support (12) such that the at least one superior arm extends from the superior support. The insertion instrument further comprises at least one inferior arm (20), (22) mounted on an inferior support (14) such that the at least one inferior arm extends from the inferior support. The superior and inferior supports (12), (14) are mechanically coupled to each other whereby: the at least one superior arm (16), (18) and the at least one inferior arm (20), (22) extend in generally a same direction such that, in use, each of the distal ends of the superior and inferior arms engage at a respective location on a modular intervertebral fusion device or component thereof; and the superior and inferior supports (12), (14) rotate relative to each other (Continued)

to provide relative rotation of: the at least one superior arm; and the at least one inferior arm, whereby there is movement together and apart of the at least one superior arm and the at least one inferior arm at their distal ends. One of: the at least one superior arm (16), (18); and the at least one inferior arm (20), (22) is unarticulated between its distal end and the respective superior or inferior support (12), (14). The other one of: the at least one superior arm (16), (18); and the at least one inferior arm (20), (22) comprises a hinge (32) between its distal end and the respective superior or inferior support. The hinge (32) rotates the distal end of the other one of the superior arm and the inferior arm towards or away from the one of the superior arm and the inferior arm.

20 Claims, 7 Drawing Sheets

(52) U.S. Cl.
CPC .............. *A61F 2002/30604* (2013.01); *A61F 2002/4622* (2013.01); *A61F 2002/4628* (2013.01)

(56) References Cited

U.S. PATENT DOCUMENTS

| | | | |
|---|---|---|---|
| 6,113,637 | A | 9/2000 | Gill et al. |
| 8,308,804 | B2 | 11/2012 | Krueger |
| 8,388,686 | B2 | 3/2013 | Aebi et al. |
| 8,465,546 | B2 * | 6/2013 | Jodaitis ................ A61F 2/0095 623/17.16 |
| 9,402,739 | B2 | 8/2016 | Weiman et al. |
| 9,526,628 | B2 | 12/2016 | Krueger |
| 9,585,765 | B2 | 3/2017 | Niemiec et al. |
| 9,801,734 | B1 | 10/2017 | Stein et al. |
| 2002/0143399 | A1 | 10/2002 | Sutcliffe |
| 2003/0187506 | A1 | 10/2003 | Ross et al. |
| 2003/0229355 | A1 | 12/2003 | Keller |
| 2004/0254644 | A1 | 12/2004 | Taylor |
| 2006/0015183 | A1 | 1/2006 | Gilbert et al. |
| 2007/0016221 | A1 | 1/2007 | Beyersdorff et al. |
| 2007/0233152 | A1 | 10/2007 | Stad et al. |
| 2007/0270957 | A1 | 11/2007 | Heinz |
| 2007/0276498 | A1 | 11/2007 | Aebi et al. |
| 2008/0082169 | A1 * | 4/2008 | Gittings ................ A61B 17/025 623/23.47 |
| 2008/0082173 | A1 | 4/2008 | Delurio et al. |
| 2008/0294260 | A1 | 11/2008 | Gray |
| 2011/0153020 | A1 | 6/2011 | Abdelgany et al. |
| 2011/0184522 | A1 | 7/2011 | Melkent et al. |
| 2013/0006357 | A1 | 1/2013 | Krueger |
| 2013/0085573 | A1 | 4/2013 | Lemoine et al. |
| 2013/0103153 | A1 | 4/2013 | Blackwell et al. |
| 2013/0158667 | A1 | 6/2013 | Tabor et al. |
| 2015/0164494 | A1 | 6/2015 | Glazer |
| 2015/0320568 | A1 | 11/2015 | Ameil et al. |
| 2016/0116396 | A1 | 4/2016 | Hunt et al. |
| 2016/0166396 | A1 | 6/2016 | McClintock |
| 2016/0213483 | A1 | 7/2016 | To et al. |
| 2016/0287403 | A1 | 10/2016 | Suddaby et al. |
| 2017/0143506 | A1 | 5/2017 | Suddaby et al. |
| 2017/0196698 | A1 | 7/2017 | Kim |
| 2017/0239063 | A1 | 8/2017 | Predick |
| 2018/0000606 | A1 | 1/2018 | Hessler et al. |
| 2018/0036141 | A1 | 2/2018 | O'Neil et al. |
| 2018/0098860 | A1 | 4/2018 | To et al. |
| 2018/0256357 | A1 | 9/2018 | To et al. |
| 2022/0015919 | A1 | 1/2022 | Reah et al. |
| 2022/0015920 | A1 | 1/2022 | Reah et al. |
| 2022/0015921 | A1 | 1/2022 | Reah et al. |

FOREIGN PATENT DOCUMENTS

| | | |
|---|---|---|
| EP | 2719360 | 4/2014 |
| WO | 00/19911 | 4/2000 |
| WO | 2004/089224 | 10/2004 |
| WO | 2006036579 A | 4/2006 |
| WO | 2013184946 | 12/2013 |
| WO | 2014093136 | 6/2014 |
| WO | 2020165586 | 8/2020 |
| WO | 2021014176 | 1/2021 |

OTHER PUBLICATIONS

Product Brochure "SYNFIX Evolution Secured Spacer System", DePuy Synthes, 2016, pp. 1-78. Copyright 2016.
International Search Report of Counterpart PCT International Application No. PCT/GB2020/051789.
International Search Report of Counterpart PCT International Application No. PCT/GB2020/051795.
Product Brochure "Aero-LL Lateral Lumbar Interbody and Fixation System", Stryker Spine, 2016, pp. 1-52.
International Search Report of Counterpart PCT International Application No. PCT/GB2019/053273.
International Search Report of Counterpart PCT International Application No. PCT/GB2019/053275.
International Search Report of Counterpart PCT International Application No. PCT/GB2019/053277.
International Search Report of Counterpart PCT International Application No. PCT/GB2020/050328.

\* cited by examiner

INSERTION INSTRUMENTS

Field of the Invention

The present invention relates to insertion instruments for inserting an intervertebral device into an intervertebral space and, more particularly but not exclusively, for inserting a modular intervertebral fusion device into an intervertebral space.

Background Art

Adjacent vertebrae in the spinal column are coupled to each other by a number of ligaments and the intervertebral disc. These anatomic structures hold the adjacent vertebrae together while allowing motion. Among these structures, the intervertebral disc functions as a cushion between the vertebrae whilst allowing for relative movement of the vertebrae. Problems with intervertebral discs arise from one or more of a range of diseases and conditions. A surgical procedure, such as spinal fusion, may be used to address such problems. The goals of spinal fusion include decompressing surrounding neural structures, re-establishing anatomic spinal alignment, and stabilising the motion segment by having one vertebral body fuse, or heal, to the adjacent vertebral body. A typical spinal fusion procedure involves partial or full removal of a problematic intervertebral disc and installation of an intervertebral device in the place of the partially or fully removed intervertebral disc in order to maintain the disc space height and alignment and facilitate the fusion of one vertebra to the next.

The anterior lumbar interbody fusion (ALIF) device is a form of intervertebral device, sometimes referred to as a cage, which is inserted into the intervertebral space by approaching the spine through the abdomen. In a typical ALIF procedure, an incision is made in one side of the abdomen. The abdominal muscles and the abdominal contents are then retracted to gain access to the spine. The disc is then removed, the disc space is properly prepared and the ALIF device is introduced by way of the incision into the thus cleared passage through the abdomen before being inserted into the intervertebral space. Compared with other procedures, such as oblique lumbar interbody fusion and posterior lumbar interbody fusion procedures, the ALIF procedure allows a larger intervertebral device to be inserted into the intervertebral space. The typical ALIF device is therefore larger than other forms of intervertebral device.

Usually, the ALIF device is held by an insertion instrument with the surgeon using the insertion instrument to introduce the ALIF device into the abdomen, guide the ALIF device through the abdomen, and then to insert the ALIF device into the intervertebral space. A known form of insertion instrument has arms which extend from the end of the insertion instrument held by the surgeon with the distal ends of the arms engaging respectively towards the superior and inferior ends of the ALIF device. The arms of the insertion instrument are movable relative to each other. Where the ALIF device is height and/or angle adjustable, the distal ends of the arms are moved by the surgeon to achieve a desired height and/or angle. Where ALIF devices of fixed but respectively different height and/or angle are being used, the distal ends of the arms are moved by the surgeon to engage at different times with ALIF devices of different height and/or angle.

Considering the ALIF procedure further and a modular ALIF implant specifically, upon insertion of an ALIF device in the intervertebral space with the insertion instrument, the ALIF device is positioned in such a manner as to ensure the superior endplate component of the ALIF device is positioned up against the inferior endplate of the superior vertebra and the inferior endplate component of the ALIF device is positioned up against the superior endplate of the inferior vertebra. With the ALIF endplates in position, an appropriately sized core component can be selected and inserted, locking into both the superior and inferior endplate components. By providing the surgeon with a selection of core components with different heights and lordotic angles, the surgeon can use the assembled ALIF device to achieve an anatomic correction of the position of the superior and inferior vertebrae relative to each other, restoring the desired intervertebral height and opening up the intervertebral foramen and thus decompressing any compressed nerve roots. In cases where there has been anterior displacement of one vertebra relative to the other, posterior pedicle screw fixation can be employed. With screws implanted, the spine can be manipulated from the posterior side whereby the superior vertebra slides over the ALIF device until the desired vertebral correction is achieved. When the desired vertebral correction is achieved, the ALIF device can be fixed to the superior vertebra using screws.

The present inventors have recognised known insertion instruments to have shortcomings. When an insertion instrument is being used where a significant lordotic angle is involved, the length of a typical insertion instrument is such that the arms may be spaced apart towards their proximal end to an extent that a larger abdominal incision is needed. A small abdominal incision is generally desirable to minimise trauma for the patient, reduce likelihood of infection and provide for ease of postoperative healing. Aside from this, known insertion instruments may be less readily used when the procedure involves the L5-S1 disc, it being noted that the L5-S1 disc is one of the most commonly fused discs. In an L5-S1 procedure, the inferior arm of the insertion instrument extends generally parallel to the sacral endplate. Where there is significant pelvic inclination, or perhaps even only moderate pelvic inclination, there is a risk of at least one of the arms colliding with the pubic symphysis.

The present invention has been devised in the light of the inventors' appreciation of the above-mentioned shortcomings. It is therefore an object for the present invention to provide an improved insertion instrument for inserting a modular intervertebral fusion device into an intervertebral space.

Statement of Invention

According to a first aspect of the present invention there is provided an insertion instrument for inserting a modular intervertebral fusion device or components thereof into an intervertebral space, the insertion instrument comprising:
  at least one superior arm mounted on a superior support such that the at least one superior arm extends from the superior support; and
  at least one inferior arm mounted on an inferior support such that the at least one inferior arm extends from the inferior support,
  wherein the superior support and the inferior support are mechanically coupled to each other whereby: the at least one superior arm and the at least one inferior arm extend in generally a same direction such that, in use, each of the distal ends of the superior and inferior arms engage at a respective location on a modular intervertebral fusion device or component thereof; and the superior and inferior supports rotate relative to each other to provide relative rotation of: the at least one superior arm; and the at least one inferior arm, whereby there is movement together and apart of the at least one superior arm and the at least one inferior arm at their distal ends, and wherein one of: the at least one superior arm; and the at least one inferior arm is unarticulated between its distal end and the respective one of the superior support and the inferior support, and wherein the other one of: the at least one superior arm; and the at least one inferior arm comprises a hinge between its distal end and the respective one of the superior support and the inferior support, the hinge rotating the distal end of the other one of the superior arm and the inferior arm towards or away from the one of the superior arm and the inferior arm.

The insertion instrument is for inserting a modular intervertebral fusion device or components thereof into an intervertebral space, for example, by way of the ALIF procedure described above. The modular intervertebral fusion device may therefore be an anterior lumbar interbody fusion device. A modular intervertebral fusion device typically provides for adjustment of height and angle, such as lordotic angle. The insertion instrument comprises at least one superior arm which is mounted on a superior support such that the at least one superior arm extends from the superior support. The insertion instrument also comprises at least one inferior arm mounted on an inferior support such that the at least one inferior arm extends from the inferior support.

The superior support and the inferior support are mechanically coupled to each other, such as by way of at least one hinge. The superior support and the inferior support are mechanically coupled such that the at least one superior arm and the at least one inferior arm extend in generally a same direction. In use, each of the distal ends of the superior and inferior arms engages at a respective location on a modular intervertebral fusion device or component thereof. More specifically, each of the distal ends of the superior and inferior arms may attach to a respective location on a modular intervertebral fusion device or component thereof. For example, and where the modular intervertebral fusion device has a superior endplate and an inferior endplate that are movable in relation to each other to provide for change in height and/or lordotic angle, the at least one superior arm may be attached at at least one respective location on a side of the superior endplate and the at least one inferior arm may be attached at at least one respective location on a side of the inferior endplate. Furthermore, the superior support and the inferior support are mechanically coupled for their relative rotation whereby there is relative rotation of: the at least one superior arm; and the at least one inferior arm. In use, the surgeon may rotate the superior support and the inferior support relative to each other with the surgeon manipulating the superior and inferior supports by hand either directly or by way of a further instrument, such as an instrument for inserting a core component between superior and inferior plates of an ALIF device when the superior and inferior plates are in the intervertebral space.

One of: the at least one superior arm; and the at least one inferior arm is unarticulated between its distal end and the respective one of the superior support and the inferior support. Furthermore, the one of the at least one superior arm and the at least one inferior arm may be substantially straight between its distal end and the respective one of the superior support and the inferior support. The other one of: the at least one superior arm; and the at least one inferior arm comprises a hinge between its distal end and the respective one of the superior support and the inferior support, the hinge rotating the distal end of the other one of the superior arm and the inferior arm towards or away from the one of the superior arm and the inferior arm. The other one of the superior arm and the inferior arm may comprise a proximal portion which extends from the respective one of the superior support and the inferior support to the hinge and a distal portion which extends from the hinge to the distal end of the arm. Each of the proximal and distal portions may be straight.

The insertion instrument may comprise a pair of superior arms which are mounted on a superior support such that the superior arms are spaced apart and extend generally parallel with each other from the superior support. The insertion instrument may also comprise a pair of inferior arms mounted on an inferior support such that the inferior arms are spaced apart and extend generally parallel with each other from the inferior support.

Alternatively, the insertion instrument may comprise one superior arm and one inferior arm. At least one of the superior and inferior arms may have the form of a frame.

If the modular intervertebral fusion device has a large angle, a distal portion of the at least one superior arm is at a correspondingly large angle to a distal portion of the at least one inferior arm. Where the superior and inferior arms in a known insertion instrument are long, as is typically required in an insertion instrument for an ALIF device, the separation between the superior arm and the inferior arm at their proximal ends, i.e. at the arm support, may be considerable. The hinge in the at least one arm according to the invention allows there to be a significant angle between the superior and inferior arms at the intervertebral device whilst allowing for reduction in an extent to which there is separation between the at least one superior arm and the at least one inferior arm at their proximal ends. Reduction in extent to which there is separation between the at least one superior arm and the at least one inferior arm at their proximal ends may allow for the abdominal incision to be smaller and less traumatic to the patient.

Where the insertion instrument is being used in the like of an L5-S1 procedure, the presence of a hinge in the at least one inferior arm reduces likelihood of the at least one inferior arm colliding with the pubic symphysis. The hinge may therefore be in each of the at least one inferior arm.

The insertion instrument may comprise a pair of superior arms which are spaced apart from each other and extend generally parallel with each other from the superior support. The pair of superior arms may extend substantially parallel with each other from the superior support. Each of the pair of superior arms may be unarticulated between its distal end and the superior support.

Alternatively, the insertion instrument may comprise one superior arm. The one superior arm may be unarticulated between its distal end and the superior support.

The insertion instrument may comprise a pair of inferior arms which are spaced apart from each other and extend generally parallel with each other from the inferior support. The pair of inferior arms may extend substantially parallel with each other from the inferior support. Each of the pair of inferior arms may comprise a hinge between its distal end and the inferior support, the hinge rotating the distal end of the inferior arm towards or away from the at least one superior arm.

Alternatively, the insertion instrument may comprise one inferior arm. The one inferior arm may comprise a hinge between its distal end and the inferior support, the hinge rotating the distal end of the inferior arm towards or away from the at least one superior arm.

As mentioned above, the superior support and the inferior support are mechanically coupled to each other to allow for the superior support and the inferior support to rotate relative to each other. Furthermore, the superior support and the inferior support may be mechanically coupled to each other to allow the superior support and the inferior support to be moved together and apart. Movement involving relative rotation and movement together and apart may be provided by way of the same mechanical coupling arrangement.

The superior support and the inferior support may rotate about a support axis which is substantially orthogonal to a longitudinal axis of the arms and substantially orthogonal to a direction of separation of the superior and inferior supports.

In addition, the superior support and the inferior support may be mechanically coupled to each other to restrict and perhaps even substantially prevent movement of the superior support and the inferior support relative to each other in a transverse direction, i.e. in a direction orthogonal to a direction of extension of arms from superior or inferior support and in a direction orthogonal to a direction of separation of the superior and inferior supports.

Alternatively or in addition, the superior support and the inferior support may be mechanically coupled to each other to restrict and perhaps even substantially prevent movement of the superior support and the inferior support relative to each other in a longitudinal direction, i.e. in the direction of extension of at least one arm from superior or inferior support.

In an alternative embodiment, the superior support and the inferior support may be mechanically coupled to each other to restrict and perhaps even substantially prevent movement of the superior support and the inferior support relative to each other in a direction of separation of the superior and inferior supports.

In addition, the superior support and the inferior support may be mechanically coupled to each other for movement of the superior and inferior supports relative to each other in a longitudinal direction. The inferior support may comprise a spring bias which is operative to drive the superior support relative to the inferior support in the longitudinal direction away from the inferior support. When the proximal and distal portions of the inferior arm are unbent such that a distance between the distal end of the inferior arm and the inferior support is of greatest extent, the spring bias may provide for alignment of the distal ends of the superior and inferior arms. When the proximal and distal portions of the inferior arm are bent, a distance between the inferior support and the distal end of the inferior arm is decreased, and the superior support may be moved relative to the inferior support against the spring bias to maintain alignment of the distal ends of the superior and inferior arms.

Nevertheless, according to the alternative embodiment, the superior support and the inferior support may be mechanically coupled to each other to allow their relative rotation and to restrict and perhaps even substantially prevent movement of the superior support and the inferior support relative to each other in a transverse direction.

The superior support and the inferior support may define inter-engaging profiles which cooperate to provide for rotation of the superior support and the inferior support relative to each other. Furthermore, the inter-engaging profiles may cooperate to provide for movement of the superior support and the inferior support together and apart.

The inter-engaging profiles may comprise a protrusion extending from one of the superior and inferior supports and a recess or perhaps even an aperture defined in the other of the superior and inferior supports, the protrusion being received in the recess or aperture to allow for at least one of: rotation; and movement of the superior support and the inferior support together and apart. In addition, the recess may have the form of a channel with the protrusion travelling along the channel to provide for movement of the superior support and the inferior support together and apart. Where an aperture is present, the aperture may have the form of a slot with the protrusion travelling along the slot to provide for movement of the superior support and the inferior support together and apart as well as relative rotation.

A first set of inter-engaging profiles may be on a first side of the superior and inferior supports and a second set of inter-engaging profiles be on a second side of the superior and inferior supports, the first and second sides facing in opposite directions. The first and second sides may be spaced apart in the transverse direction.

The superior and inferior supports may not be attached to each other by other than at least one set of inter-engaging profiles.

The inter-engaging profiles may be configured to allow for disengagement of the superior and inferior supports from each other and for separation of the superior and inferior supports from each other. A first part of the inter-engaging profiles may be movable away from a second part of the inter-engaging profiles to allow for such disengagement and separation. More specifically, the first and second parts may be comprised in one of the superior and inferior supports, such as the inferior support. Furthermore, the first and second parts may be shaped to accommodate and engage with a third part comprised in the other of the superior and inferior supports, such as the superior support. Engagement of the third part with the first and second parts may present a barrier to separation of the superior and inferior supports, such as by each of the first and second parts fitting around the third part. When the first part is moved away from the second part, such as against a spring bias, the relative disposition of the first and second parts may allow for release of the third part from the first and second parts. More specifically, a user may withdraw the third part from between the first and second parts by moving the superior and inferior supports apart from each other.

At least one arm may be mounted, and more specifically mounted at its proximal end, on each of the superior and inferior supports. The arm may be mounted such that the arm is substantially immovably relative to its respective superior or inferior support with the exception of rotation of the arm relative to the respective superior or inferior support and about the longitudinal axis of the arm. As described below, rotation of the arm relative to the support about the longitudinal axis of the arm may allow for the distal end of the arm to lock to the modular intervertebral fusion device.

Alternatively, and in particular where the insertion instrument comprises one superior arm, the superior arm may be immovably mounted on the superior support and more specifically may be integrally formed with the superior support.

Alternatively or in addition, and in particular where the insertion instrument comprises one inferior arm, the inferior arm may be immovably mounted on the inferior support and more specifically may be integrally formed with the inferior support.

Where the insertion instrument comprises a pair of each of superior and inferior arms as described above, a first superior arm and a first inferior arm may lie in substantially a first plane and a second superior arm and a second inferior arm may lie in substantially a second plane, the first and second planes being substantially parallel. As described above, the hinge rotates the distal end of one of the superior arm and the inferior arm towards or away from the other one of the superior arm and the inferior arm. The hinge may therefore rotate about a hinge axis and more specifically a transverse axis which extends between the first and second planes and more specifically extends substantially orthogonally to the first and second planes.

Where the superior and inferior supports rotate relative to each other about a support axis, the support axis may be substantially parallel to the hinge axis.

The hinge may be free to rotate about its axis whereby the hinge lacks the like of a lock for holding a distal portion of the arm at a set angle to a proximal portion of the arm.

The hinge may be located closer to the distal end of the arm than to the respective one of the superior and inferior supports. More specifically, the hinge may be 20 mm to 100 mm from the distal end of the arm. Having the hinge between 50 mm and 70 mm from the distal end of the arm has been found to provide for effective reduction in risk of collision with the pubic symphysis for a typical patient. Where the hinge is thus spaced from the distal end of the arm, the arm may be of a length of 250 mm to 350 mm and typically 300 mm. The superior and inferior arms may be of substantially the same length.

The distal end of an arm may be tapered. Alternatively or in addition, the distal end of an arm may be shaped to be snugly received in a recess defined in the intervertebral device. Each of the superior and inferior arms may thus be attached to a different location on the intervertebral device. More specifically, the at least one superior arm may be received in a recess defined in a superior endplate of the intervertebral device and the at least one inferior arm may be received in a recess defined an inferior endplate of the intervertebral device.

The distal end of an arm may be configured to resist detachment from the intervertebral device. Where the distal end of the arm is received in a recess, resistance to detachment may be by way of profiles which releasably engage with each other when the distal end is received in the recess. As described above, rotation of the arm relative to the support about the longitudinal axis of the arm may allow for the distal end of the arm to lock to the modular intervertebral fusion device. Further to this, the distal end of the arm and the recess may define cooperating profiles which allow for insertion of the distal end of the arm into the recess and which present resistance to withdrawal of the distal end of the arm from the recess after the arm has been rotated relative to the support about the longitudinal axis of the arm when the distal end of the arm is in the recess.

In an alternative embodiment, the insertion instrument may comprise at least one of: one superior arm only; and one inferior arm only. In view of the insertion instrument lacking two arms mounted on at least one of the superior support and the inferior support, the one superior arm may be configured to grip oppositely directed sides of a superior endplate component instead of engaging with the superior endplate component by rotation of each of two arms. Alternatively or in addition, the one inferior arm may be configured to grip oppositely directed sides of an inferior endplate component.

Oppositely directed sides of the endplate component may be gripped by a gripping arrangement. The gripping arrangement may comprise first and second sprung fingers which extend from a distal end of a respective arm, the first and second sprung fingers spaced apart to sufficient extent to receive an endplate component therebetween. The first and second fingers may be sprung, for example by way of the material from which they are formed such that they are inherently sprung, to increase an extent of separation therebetween towards distal ends of the first and second fingers. An endplate component may be received readily between the first and second fingers in such disposition.

The gripping arrangement may further comprise a compression mechanism which releasably engages with the first and second fingers to compress the first and second fingers together towards their distal ends and against the spring bias. The endplate component may be gripped by the first and second fingers when the compression mechanism has engaged with the first and second fingers.

The compression mechanism may comprise a compression body which is movably attached to its respective arm, the compression body mounted on the arm for movement along the arm. Movement of the compression body along the arm may provide for compression and release from compression of the first and second fingers. When the compression body is moved away from the respective one of the superior and inferior supports, the compression body may bear against the first and second fingers to compress the first and second fingers together. Each of the first and second fingers may define a shoulder against which the compression body bears to effect deflection of the respective finger. Movement of the compression body towards the respective one of the superior and inferior supports may release the first and second fingers from compression.

The arm may comprise a compression mechanism driving arrangement which is supported on its respective arm for movement relative to the arm. The compression mechanism driving arrangement may comprise a first driving member and a second driving member which are hingedly coupled to each other. The first driving member may be coupled at its proximal end to the respective one of the superior support and the inferior support and may be hingedly coupled at its distal end to a proximal end of the second driving member. The second driving member may be attached to the compression mechanism whereby the compression mechanism moves with the second driving member. Movement of the first driving member may cause the second driving member to move back and forth along the arm whereby the compression body moves between a first and second finger compressing position and a first and second finger releasing position.

As described above, the insertion instrument is for inserting an intervertebral device or components thereof. Therefore, and according to a second aspect of the present invention, there is provided an intervertebral device insertion assembly comprising an insertion instrument according to the first aspect and an intervertebral device or components thereof, the intervertebral device being configured for attachment of each of the superior and inferior arms at respective spaced apart locations on the intervertebral device or on components thereof.

The intervertebral device may be configured for attachment by way of a recess defined in the intervertebral device or in components thereof for each arm of the insertion instrument. The intervertebral device may comprise a superior endplate and an inferior endplate, the superior endplate defining a respective recess for each of the at least one superior arm, and the inferior endplate defining a respective recess for each of the at least one inferior arm. Where the insertion instrument comprises a pair of each of superior and inferior arms, each of the superior endplate and the inferior endplate may define a pair of recesses, the recesses in a pair of recesses being spaced apart in the transverse direction. Alternatively, and where the insertion instrument comprises one superior arm and one inferior arm, the one superior arm may grip the superior endplate as described above and the one inferior arm may grip the inferior endplate as described above.

Further embodiments of the second aspect of the present invention may comprise one or more features of the first aspect of the present invention.

According to a third aspect of the present invention, there is provided a method of inserting a modular intervertebral fusion device into an intervertebral space by way of an insertion instrument, the insertion instrument comprising at least one superior arm mounted on a superior support such that the at least one superior arm extends from the superior support, and at least one inferior arm mounted on an inferior support such that the at least one inferior arm extends from the inferior support, the superior support and the inferior support mechanically coupled to each other whereby the at least one superior arm and the at least one inferior arm extend in generally a same direction, the method comprising:

engaging each of distal ends of the superior and inferior arms at a respective location on a modular intervertebral fusion device;

rotating the superior and inferior supports relative to each other to provide relative rotation of: the at least one superior arm; and the at least one inferior arm, whereby there is movement together and apart of the superior arm and inferior arm at their distal ends, and introducing the modular intervertebral fusion device or components thereof, for example, superior and inferior endplates of the modular intervertebral fusion device, into the intervertebral space by way of the insertion instrument, wherein one of: the at least one superior arm; and the at least one inferior arm is unarticulated between its distal end and the respective one of the superior support and the inferior support, and wherein the other one of: the at least one superior arm;

and the at least one inferior arm comprises a hinge between its distal end and the respective one of the superior support and the inferior support, the hinge rotating the distal end of the other one of the superior arm and the inferior arm towards or away from the one of the superior arm and the inferior arm.

Embodiments of the third aspect of the present invention may comprise one or more features of the first or second aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

Figures 1A, 1B:
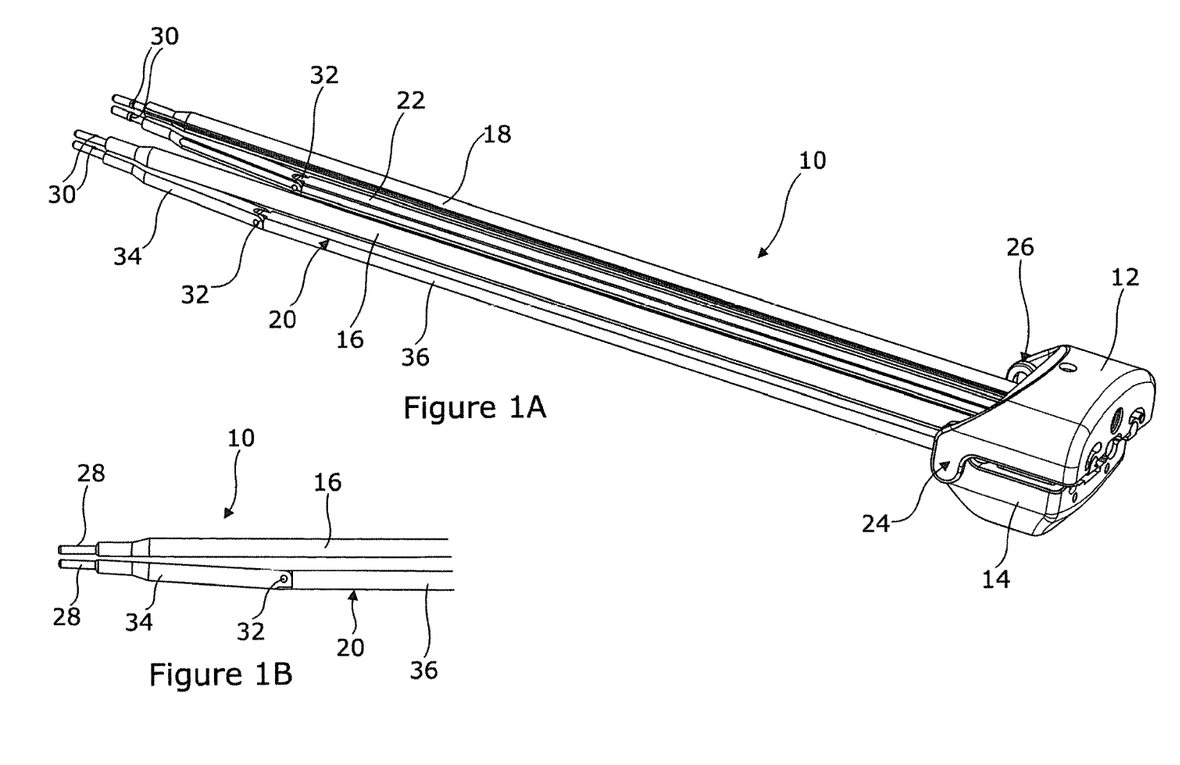
FIG. 1A is a perspective view of an insertion instrument according to a first embodiment of the present invention.
FIG. 1B is a side view of the distal ends of the arms of the insertion instrument of FIG. 1A.

A perspective view of an insertion instrument 10 according to a first embodiment of the present invention is shown in FIG. 1A. The insertion instrument 10 comprises a superior support 12, an inferior support 14, a pair of superior arms consisting of a first superior arm 16 and a second superior arm 18, and a pair of inferior arms consisting of a first inferior arm 20 and a second inferior arm 22. The pair of superior arms 16, 18 are mounted on the superior support 12 such that they extend from spaced apart locations on the superior support and such that the superior arms are substantially parallel. The pair of inferior arms 20, 22 are mounted on the inferior support 14 such that they extend from spaced apart locations on the inferior support 14 and such that the inferior arms are substantially parallel. Each of the four arms 16, 18, 20, 22 is mounted on its respective support for rotation of the arm relative to the support and about the longitudinal axis of the arm; otherwise, the arm is immovable in relation to the support. The superior support 12 and the inferior support 14 are mechanically coupled to each other by a first hinge mechanism 24 and a second hinge mechanism 26. The first hinge mechanism 24 is at a first side of the superior and inferior supports 12, 14 and the second hinge mechanism 26 is at a second side of the superior and inferior supports, the first and second sides facing in opposite directions. The first and second hinge mechanisms 24, 26 are described further below with reference to FIGS. 2A and 2B.

The first and second hinge mechanisms 24, 26 allow the superior support 12 and the inferior support 14 to rotate relative to each other and for the superior and inferior supports to be moved together and apart whilst restricting other relative movement of superior and inferior supports such as in the longitudinal direction of the arms, or in the direction of separation of the superior arms or of the inferior arms. The superior support 12 and the inferior support 14 thus rotate about a support axis which is substantially orthogonal to a longitudinal axis of the arms 16, 18, 20, 22 and substantially orthogonal to a direction of separation of the superior and inferior supports. The pair of superior arms 16, 18 moves with the superior support 12 and the pair of inferior arms 20, 22 moves with the inferior support 14. Relative rotation of the superior and inferior supports 12, 14 therefore causes the pair of superior arms 16, 18 and the pair of inferior arms 20, 22 to rotate relative each other. Also, movement of the superior and inferior supports 12, 14 together and apart moves the pair of superior arms 16, 18 and the pair of inferior arms 20, 22 together and apart. As will become clear from the description provided below with reference to FIGS. 2A and 2B, the first and second hinge mechanisms 24, 26 allow for relative rotation of superior and inferior supports 12, 14 at the same time as movement of the superior and inferior supports 12, 14 together and apart.

Mechanical coupling of the superior and inferior supports 12, 14 by way of the first and second hinge mechanisms 24, 26 is such that the pair of superior arms 16, 18 and the pair of inferior arms 20, 22 extend generally in the same direction. Although FIG. 1A shows the pair of superior arms 16, 18 as parallel to the pair of inferior arms 20, 22, increased separation of the superior and inferior supports 12, 14 accompanied by relative rotation of the superior and inferior supports causes the pair of superior arms and the pair of inferior arms to be angled to each other. Nevertheless, the pair of superior arms 16, 18 and the pair of inferior arms 20, 22 extend generally in the same direction despite the angulation.

A side view of the distal ends of the arms of the insertion instrument 10 of FIG. 1A is shown in FIG. 1B. The first superior arm 16 and the first inferior arm 20 can be seen in FIG. 1B to be slightly spaced apart and extending in parallel. As described above, the superior and inferior supports 12, 14 can be manipulated by the surgeon to increase their separation and to angle the pair of superior arms 16, 18 and the pair of inferior arms 20, 22 relative to each other. Considering FIG. 1B further, each of the four arms tapers towards its distal end with a distal portion 28 having the form of a cylinder. With reference to the superior endplate 50 and the inferior endplate 60 shown in FIG. 3, each distal portion 28 is sized and shaped to be a snug fit in a respective recess 52, 54, 62, 64 proved in the superior and inferior endplates 50, 60 of an anterior lumbar interbody fusion (ALIF) device whereby the superior and inferior endplates are supported by the four arms. The superior and inferior endplates can therefore be manipulated by the surgeon by movement of the superior and inferior supports 12, 14 while the superior and inferior endplates 50, 60 are supported properly by the four arms. Returning to FIG. 1A, a protrusion 30 extends from the surrounding surface of each distal portion 28. Each of the superior and inferior endplates of the ALIF device defines a pair of recesses 52, 54 and 62, 64 in the anterior side of the endplate with the recesses in each pair spaced apart in the transverse direction. Each surface of the endplate that defines the recess 52, 54, 62, 64 has a linear channel in the wall of the recess which extends from the mouth of the recess into the depth of the recess. Furthermore, the furthest most reach of the linear channel is terminated by a circumferentially extending portion of channel in the wall of the recess. When the distal portion 28 is inserted into a corresponding recess 52, 54, 62, 64 in an endplate, the protrusion 30 is received in the linear channel in the wall of the recess and travels along the linear channel as the distal portion 28 is progressively further received in the recess. When the distal portion 28 is fully received in the recess 52, 54, 62, 64, the protrusion 30 is at the furthest most reach of the linear channel. The surgeon then rotates each arm around its longitudinal axis within the support whereby the protrusion 30 travels along the circumferentially extending portion of channel at the end of the linear channel. Reception of the protrusion 30 in the circumferentially extending portion of channel presents resistance to withdrawal of the distal portion 28 of the arm from the recess 52, 54, 62, 64 in the endplate. The four arms are thus securely attached to respective locations on the endplates.

Considering FIGS. 1A and 1B further, each of the first and second inferior arms 20, 22 has a hinge 32 between 50 mm and 70 mm from the distal end of the arm. The hinge 32 allows for a distal portion 34 between the distal end and the hinge and a proximal portion 36 between the hinge and the inferior support to rotate relative to each other. The hinge 32 rotates about a hinge axis which is substantially parallel to the support axis whereby the distal portion 34 of the first inferior arm 20 rotates towards and away from the first superior arm 16 and the distal portion 34 of the second inferior arm 22 rotates towards and away from the second superior arm 18. In contrast, the first and second superior arms 16, 18 are unarticulated.

The insertion instrument is formed from a standard surgical instrument metal, such as stainless steel. Alternatively, the insertion instrument is formed from a plastics material, such as polycarbonate or nylon. An insertion instrument formed from a plastics material is typically for single use before disposal.

Figure 2A:
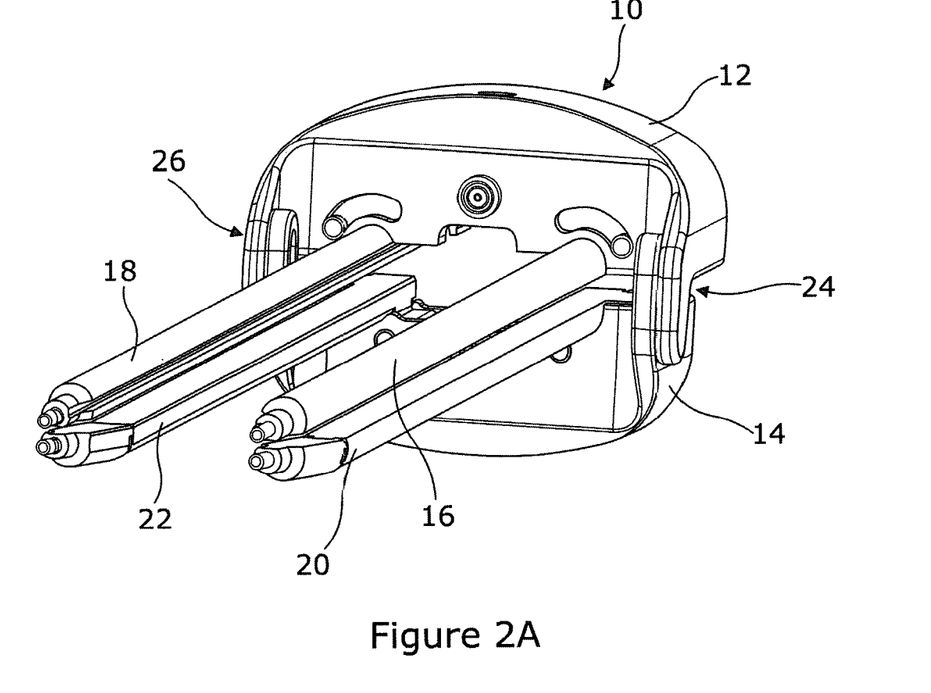
FIG. 2A is a perspective view of the insertion instrument of FIG. 1A looking from the distal ends of the arms towards the superior and inferior supports.

FIG. 2A shows a perspective view of the insertion instrument 10 of FIG. 1A looking from distal ends of the arms towards the superior and inferior supports 12, 14. As can be seen from FIG. 2A, the pair of superior arms 16, 18 are mounted on the superior support 12 such that they move with the superior support and the pair of inferior arms 20, 22 are mounted on the inferior support 14 such that they move with the inferior support. The four arms are mounted on the superior and inferior supports 12, 14 such that the four arms extend between the first and second hinge mechanisms 24, 26.

Figure 2B:
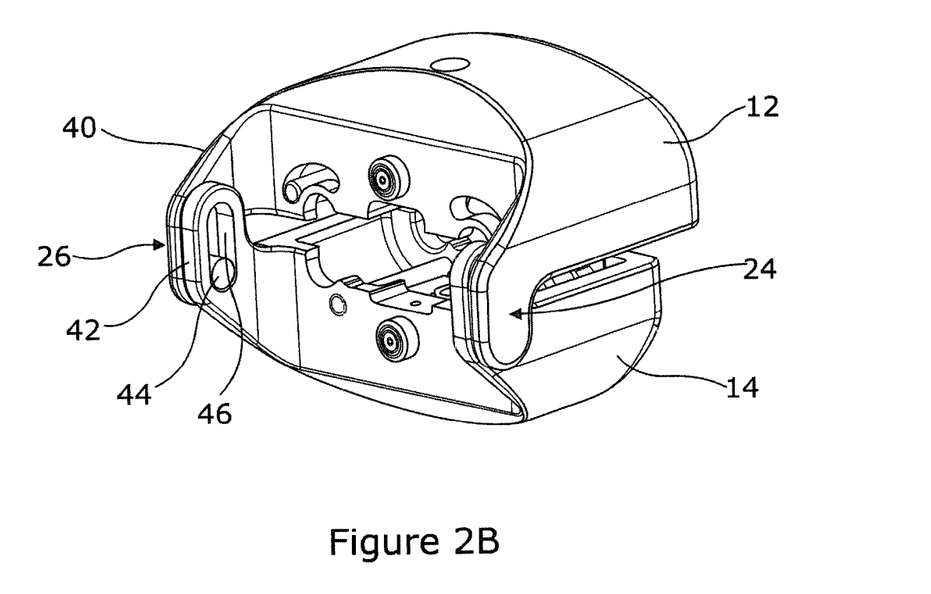
FIG. 2B is the perspective view of FIG. 2A with the arms removed.

The perspective view of FIG. 2A with the arms removed is shown in FIG. 2B. A superior support lug 40 extends from one side of a main body of the superior support 12 in the direction of the arms and an inferior support lug 42 extends from the same one side of a main body of the inferior support 14 in a direction of the arms. The superior support lug 40 and the inferior support lug 42 overlap. The same structure of superior and inferior support lugs is provided at the other side of the superior and inferior supports. The second hinge mechanism 26 is constituted by a cylindrical protrusion 44 which extends towards the arms from the superior support lug 40 and a slot 46 defined in the inferior support lug 42. The slot 46 extends in a direction of separation of the pair of superior arms and the pair of inferior arms from each other. The protrusion 44 is received in the slot 46 whereby the protrusion can rotate in the slot and also travel along the slot. The first hinge mechanism 24 is constituted in the same way with the exception that it is the mirror image of the second hinge mechanism 26 such that, for example, the slots are in registration with each other and the protrusions are aligned and extend towards each other. The first hinge and second hinge mechanisms 24, 26 thus allow the superior and inferior supports 12, 14 to be rotated relative to each other and for the superior and inferior supports to be moved together and apart.

Figure 3:
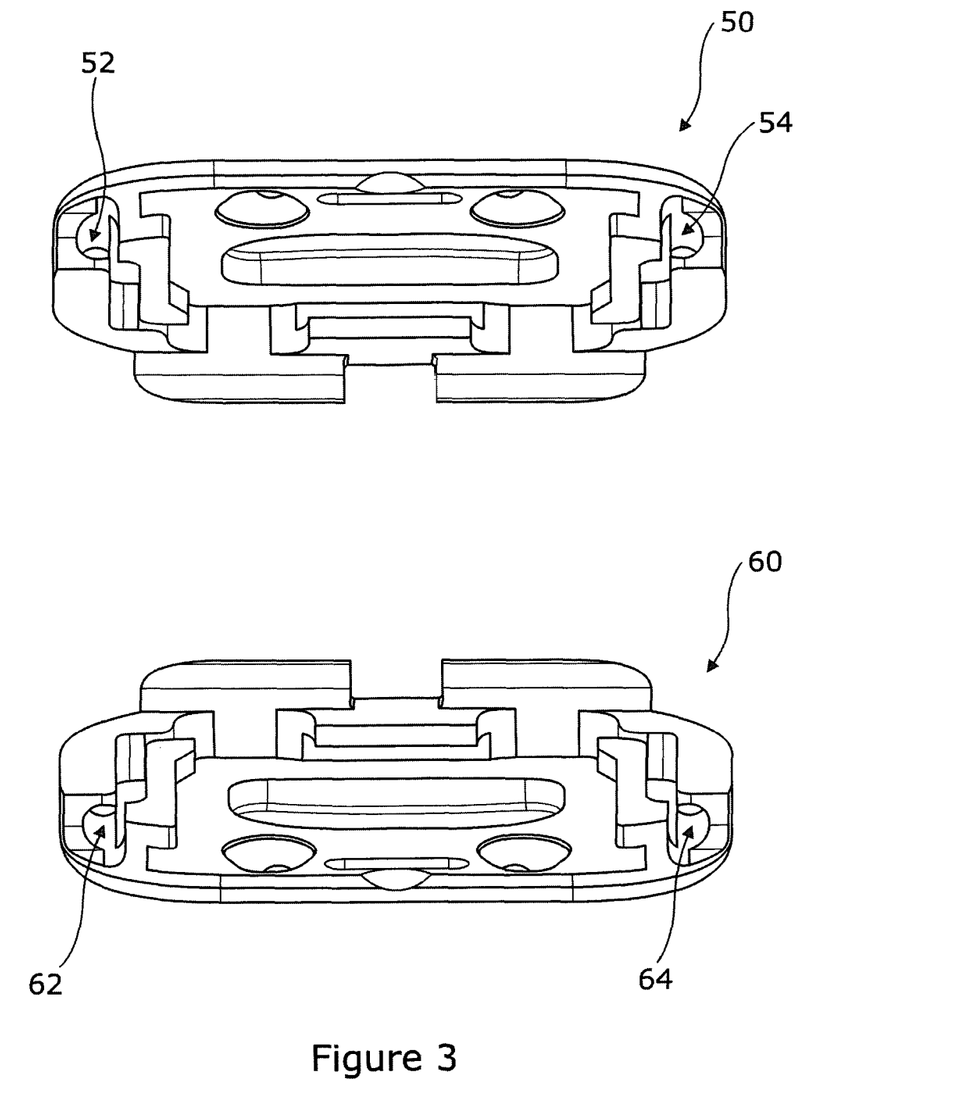
FIG. 3 shows superior and inferior endplates of an anterior lumbar interbody fusion device configured for use with the insertion instruments of FIGS. 1A and 5A.

As described above, the superior and inferior endplates 50, 60 are attached to their respective pair of arms 16, 18, 20, 22 by insertion into and locking in of each arm in its respective recess 52, 54, 62, 64. When the superior and inferior endplates 50, 60 have thus been attached to the insertion instrument 10, the surgeon uses the insertion instrument to introduce the superior and inferior endplates to the patient's intervertebral space. When the superior and inferior endplates are in the intervertebral space, the surgeon manipulates the superior and inferior supports 12, 14 of the insertion instrument 10 to achieve a desired separation between the superior and inferior endplates and hence height of intervertebral device and a desired angle between the superior and inferior endplates, whether the angle is lordotic and/or transverse. As described above, the hinges 32 in the inferior arms 20, 22 reduce extent to which there is separation between the pair of superior arms 16, 18 and the pair of inferior arms 20, 22 at their proximal ends to thereby allow for the abdominal incision, by which the superior and inferior endplates are admitted, to be smaller. Where the insertion instrument 10 is being used in the like of an L5-S1 procedure, the disposition of the arms by virtue of the hinges reduces likelihood of the pair of inferior arms colliding with the pubic symphysis.

When the superior and inferior endplates 50, 60 are held by the insertion instrument 10 in the intervertebral space, sizing trials are carried out to determine desired height and angle for the intervertebral device. Such sizing trials are carried out in accordance with a known approach and are therefore described no further. When desired height and angle have been determined, a core of appropriate height and angle is selected and inserted between the superior and inferior endplates 50, 60 being held by the insertion instrument 10 in the intervertebral space. Core insertion is described below with reference to FIG. 4. When the core has been inserted, the surgeon rotates each of the four arms 16, 18, 20, 22 in the opposite direction to the direction to achieve locking of the arms in their recesses 52, 54, 62, 64. Upon such rotation of an arm, the protrusion 30 on the arm travels back along the circumferentially extending portion of channel until the protrusion reaches the linear channel defined in the wall of the recess. The protrusion 30 is thus positioned so that it may travel back along the linear channel to thereby allow for the distal end of the arm bearing the protrusion to be withdrawn from the recess. The insertion instrument 10 is thus detached from the superior and inferior endplates 50, 60 leaving the superior and inferior endplates with core in place in the intervertebral space. The insertion instrument 10 is then withdrawn from the patient's body through the incision that admitted the insertion instrument at the start of the surgical procedure.

Figure 4:
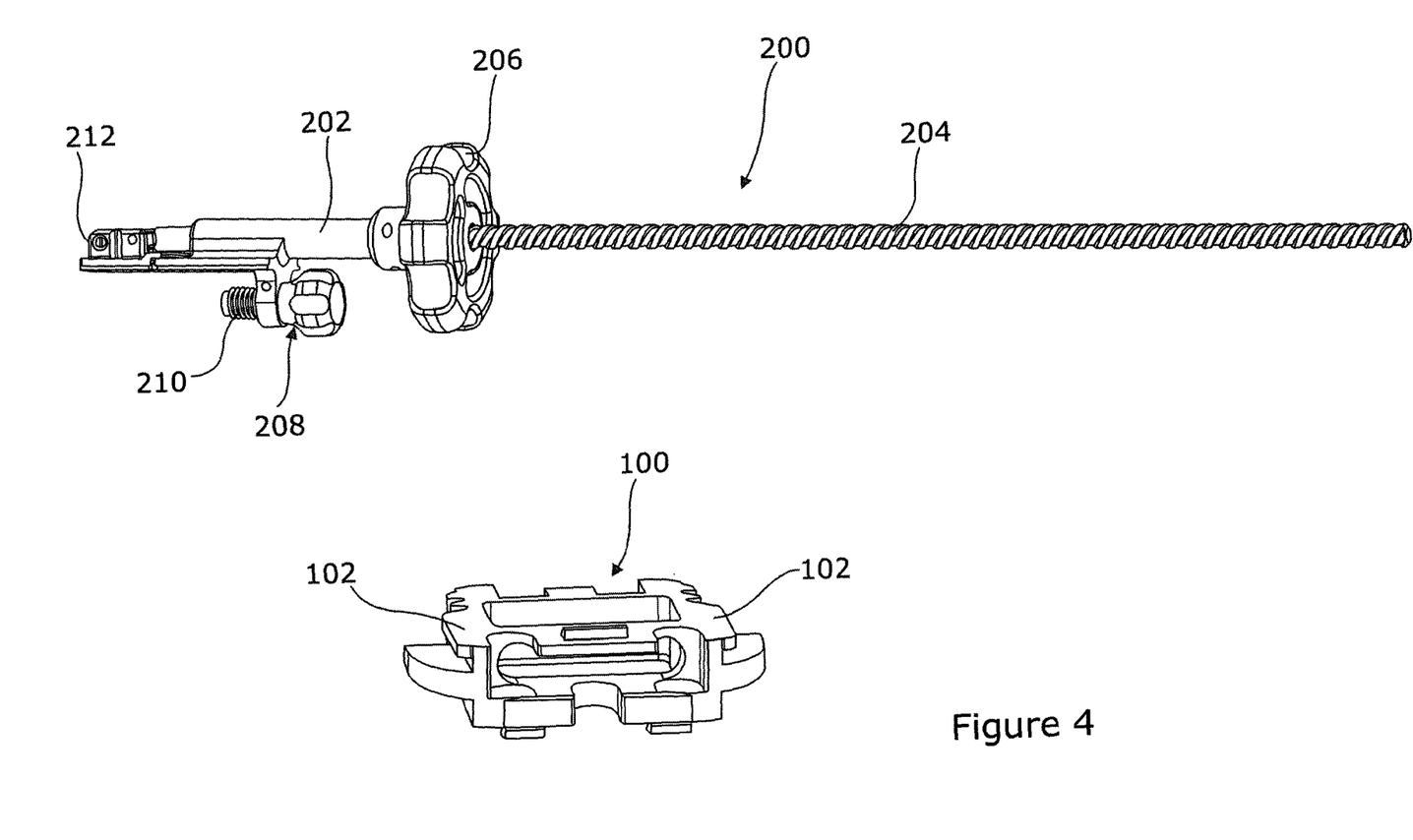
FIG. 4 shows a perspective view of a core inserter and a core to be inserted with the core inserter.

As mentioned above, a selected core is inserted between the superior and inferior endplates 50, 60 while they are held by the insertion instrument 10 in the intervertebral space. FIG. 4 shows a core 100 to be inserted and a core inserter 200 which is used in conjunction with the insertion instrument 10 to insert the core. The core 100 has an elongate protrusion 102 at each transverse side at the superior surface of the core with each elongate protrusion 102 extending in the anterior-posterior direction. The core inserter 200 comprises a core inserter support 202 and an elongate cylindrical member 204. A core inserter knob 206 is rotatably mounted on the core inserter support 202. The elongate cylindrical member 204 threadedly engages with the core inserter knob 206 whereby the cylindrical member moves through the core inserter support upon rotation of the core inserter knob 206 on the core inserter support 202. The core inserter support 202 comprises an attachment mechanism 208 which enables the core inserter support 202 to be removably and threadedly attached to the superior or inferior support 12, 14 of the insertion instrument 10 and such that the cylindrical member 204 is directed between the pair of superior arms 16, 18 and the pair of inferior arms 20, 22 of the insertion instrument 10. Considering the attachment mechanism 208 further it comprises a screw member 210 which threadedly engages with a bore defined in the anterior face of the superior or inferior support 12, 14.

As a first step during the core insertion process, the core 100 is positioned between the superior and inferior supports 12, 14 of the insertion instrument 10 and such that the elongate protrusions 102 are received in respective channels defined by the superior support 12. Next the core inserter 200 is attached by way of the attachment mechanism 208 to the superior or inferior support 12, 14 and such that the operative end 212 of the cylindrical member 204 is directed between the pair of superior arms 16, 18 and the pair of inferior arms 20, 22. The operative end 212 of the cylindrical member 204 therefore abuts against the core 100 supported by the superior support 12. The surgeon rotates the core inserter knob 206 to increase the reach of the operative end 212 of the cylindrical member 204 between the pairs of arms to thereby push the supported core 100 towards the distal ends of the arms of the insertion instrument. Facing surfaces of the superior pair of arms each define a channel with each channel in registration with a respective one of two core supporting channels defined by the superior support. The core 100 is therefore supported by the superior pair of arms as the core is driven by the core inserter 200 towards the distal ends of the arms. When the core 100 reaches the superior and inferior endplates 50, 60 held by the insertion instrument 10, the surgeon continues to rotate the core inserter knob 206 to push the core between the superior and inferior endplates 50, 60. As the core is received between superior and inferior endplates 50, 60, surface profiles on the core inter-engage with cooperating surface profiles on the superior and inferior endplates to lock the superior and inferior endplates together and such that the desired height and angle, as determined by the core, are achieved.

Figure 5A:
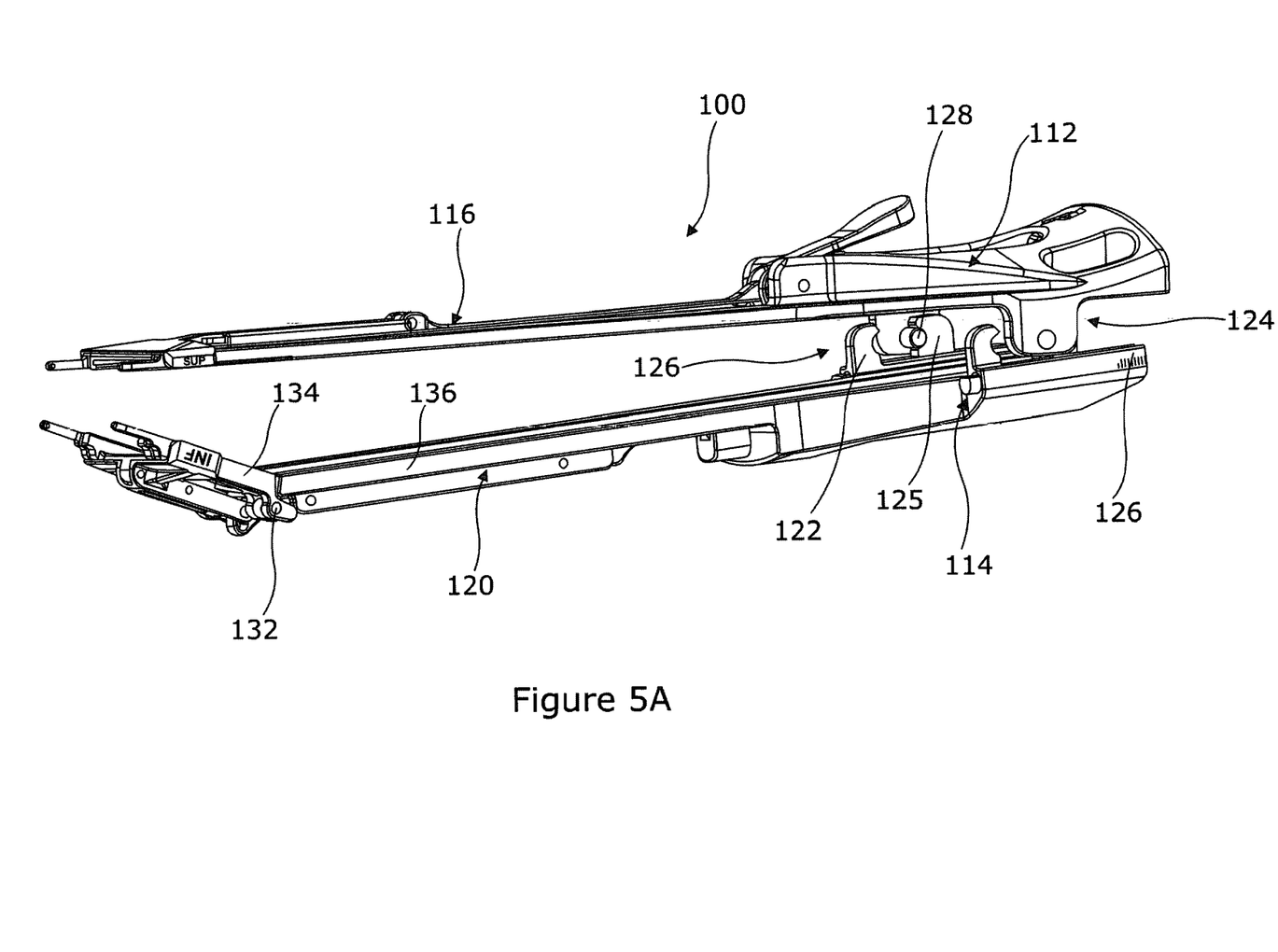
FIG. 5A is a perspective view of an insertion instrument according to a second embodiment of the present invention.

A perspective view of an insertion instrument 100 according to a second embodiment of the present invention is shown in FIG. 5A. The insertion instrument 100 comprises a superior support 112, an inferior support 114, one superior arm 116 and one inferior arm 120. Each of the superior arm 116 and the inferior arm 120 is generally rectangular when viewed in plan and is of the form of a frame. The superior arm 116 is integrally formed with and such that it extends from the superior support 112. The inferior arm 120 is integrally formed with and such that it extends from the inferior support 114. The superior support 112 and the inferior support 114 are mechanically coupled to each other by a first hinge mechanism 124 and a second hinge mechanism 126. The first hinge mechanism 124 is at a first side of the superior and inferior supports 112, 114 and the second hinge mechanism 126 is at a second side of the superior and inferior supports, the first and second sides facing in opposite directions.

The first and second hinge mechanisms 124, 126 allow the superior support 112 and the inferior support 114 to rotate relative to each other while restricting their movement together and apart and in the transverse direction. The first and second hinge mechanisms 124, 126 also allow for movement of the superior support 112 and the inferior support 114 relative to each other in the longitudinal direction, albeit with such movement impeded by spring bias as described further below. The superior support 112 and the inferior support 114 thus rotate about a support axis which is substantially orthogonal to a longitudinal axis of the first and second arms 116, 120, and substantially orthogonal to a direction of separation of the superior and inferior supports. The superior arm 116 moves with the superior support 112 and the inferior arm 120 moves with the inferior support 114. Relative rotation of the superior and inferior supports 112, 114 therefore causes the superior arm 116 and the inferior arm 120 to rotate relative each other. Also, movement of the superior and inferior supports 112, 114 relative to each other in the longitudinal direction moves the superior arm 116 and the inferior arm 120 relative to each other in the longitudinal direction.

Considering FIG. 5A further, the inferior arm 120 has a hinge 132 between 50 mm and 70 mm from the distal end of the arm. The hinge 132 allows for a distal portion 134 between the distal end and the hinge 132 and a proximal portion 136 between the hinge 132 and the inferior support to rotate relative to each other. The hinge 132 rotates about a hinge axis which is substantially parallel to the support axis whereby the distal portion 134 of the inferior arm 120 rotates towards and away from the superior arm 116. In contrast, the superior arm 116 is unarticulated.

As described above, mechanical coupling of the superior and inferior supports 112, 114 by way of the first and second hinge mechanisms 124, 126 is such that the superior arm 116 and the inferior arm 120 extend generally in the same direction. The first and second hinge mechanisms 124, 126 are of the same form and function. Each hinge mechanism 124, 126 comprises first and second parts 122, 125, with the first part 122 integrally formed with the inferior support 114 whereby the first part 122 is immovably mounted on the inferior support. The second part 125 is mounted the inferior support 114 for movement relative to the inferior support in the longitudinal direction. The disposition of the first and second parts 122, 125 is such that movement of the second part 125 moves the second part towards or away from the first part 122. Each hinge mechanism 124, 126 further comprises a spring 126 which is mounted in the inferior support 114 such that its spring bias urges the second part 125 towards the first part 122. The opposing faces of the first and second parts 122, 125 each define a recess. Each hinge mechanism 124, 126 further comprises a third part in the form of a cylindrical protrusion 128 which is integrally formed with the superior support 112. Each cylindrical protrusion 128 is mounted on an integrally formed lug which extends from the superior support 112. The cylindrical protrusions 128 of the first and second hinge mechanisms 124, 126 extend towards each other on the inferior support facing side of the superior support and such that they are in registration with each other. Relative rotation of the superior and inferior supports 112, 114 is about the two cylindrical protrusions 128. Each cylindrical protrusion 128 is received between a respective pair of first and second parts 122, 125. The bias exerted by the spring 126 urges the second part 125 towards the first part 122 such that the recesses defined by the opposing faces of the first and second parts 122, 125 fit around the cylindrical protrusion 128. Each cylindrical protrusion 128 is thus held between its respective pair of first and second parts 122, 125.

When the lower arm 120 is unbent the lower arm is at maximum reach. When the second part 125 is urged to greatest extent towards the first part 122, the superior support 112 and superior arm 116 are thrust forward to maximum extent relative to the inferior support 114 and inferior arm 120 whereby the distal end of the superior arm 116 is aligned with the distal end of the inferior arm 120. When the lower arm 120 is bent, the reach of the lower arm is reduced whereby the distal ends of the superior and inferior arms 116, 120 are misaligned. The superior and inferior arms 116, 120 are brought back into alignment by pulling the superior support 112 back against the sprung biased second parts 125 whereby the superior support 112 and superior arm 116 are pulled backwards relative to the inferior support 114 and inferior arm 120. Despite the first and second parts 122, 125 being now spaced apart from each other and such that the cylindrical protrusion 128 is no longer in contact with the first part (as shown in FIG. 5A), the recess defined in the face of the second part 125 presents resistance to separation of the superior and inferior supports from each other. Should the user wish to separate the superior and inferior supports from each other, the second parts 125 are held against the spring bias in their pulled back position and the superior support 112 is moved such that the cylindrical protrusions 128 are moved away from the second parts 125 while being spaced apart from the first parts 122. The cylindrical protrusions 128 may then be withdrawn from between the pairs of first and second parts 122, 125 to allow for separation of the superior and inferior supports from each other.

Figure 5B:
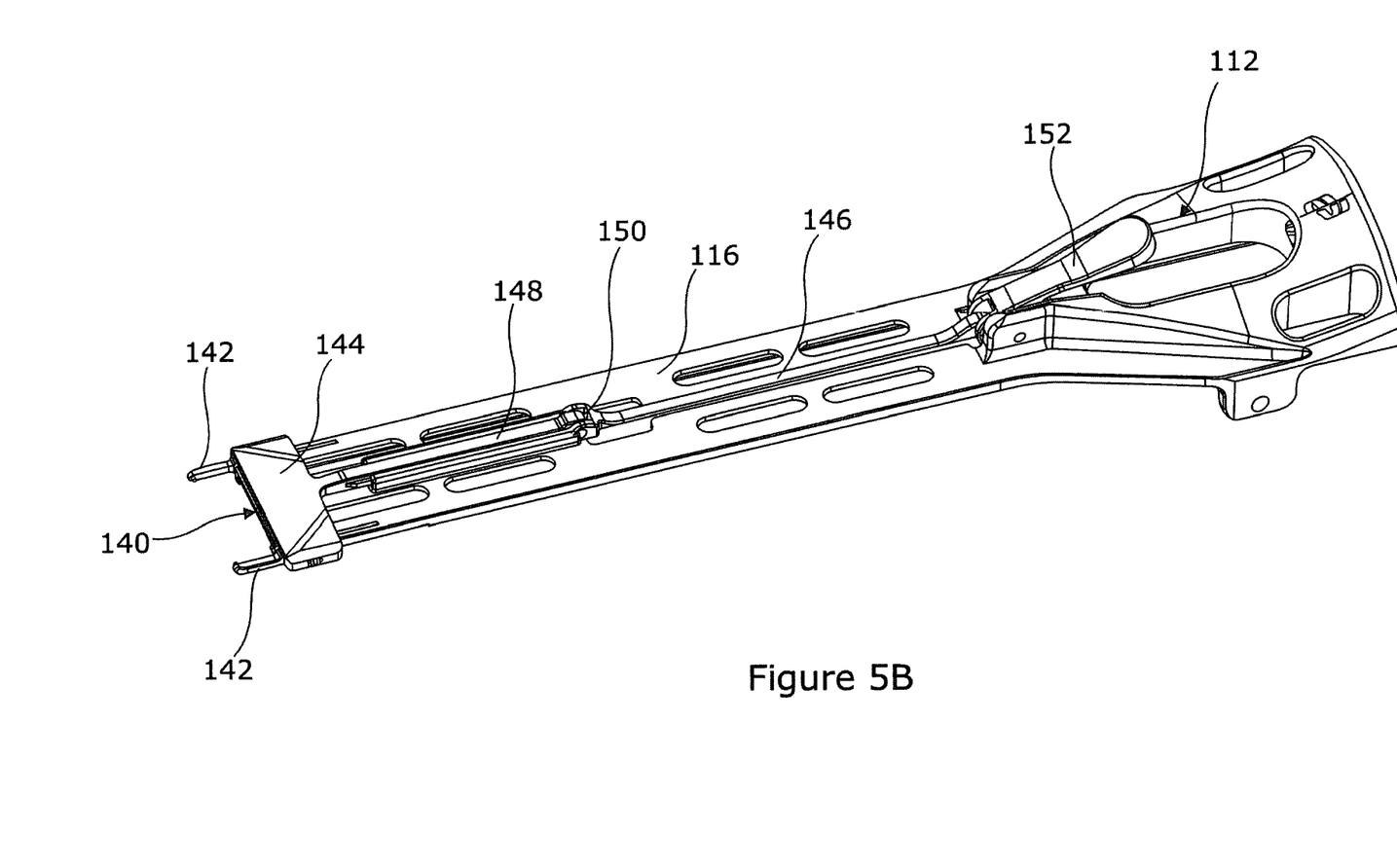
FIG. 5B is a view of a superior part of the insertion instrument of FIG. 5A.

A view of a superior part of the insertion instrument of FIG. 5A is shown in FIG. 5B. The superior part comprises the previously described superior support 112 and superior arm 116, amongst other components. The superior part further comprises an endplate gripping arrangement 140. The endplate gripping arrangement 140 comprises first and second sprung fingers 142 which extend from a distal end of the superior arm 116. The first and second sprung fingers 142 are mounted such that they are spaced apart to sufficient extent to receive an endplate component therebetween. The first and second fingers 142 are sprung by virtue of the material from which they are formed such that they are inherently sprung and such that the spring bias urges the distal ends of the first and second fingers apart. A superior endplate component can be received readily between the first and second fingers in this condition. The gripping arrangement 140 further comprise a compression mechanism which releasably engages with the first and second fingers 142 to compress the first and second fingers together towards their distal ends and against their spring bias. The superior endplate component is gripped by the first and second fingers 142 when the compression mechanism has engaged with the first and second fingers.

The compression mechanism comprises a compression body 144 which is movably attached to the superior arm 116 for movement along the superior arm. Furthermore, the compression body 144 is disposed on the superior arm such that movement of the compression body away from the superior support 112 causes the compression body to bear against a shoulder defined by each of the first and second fingers 142. Bearing of the compression body 144 against the shoulders defined by the first and second fingers 142 causes the first and second fingers to deflect towards each other against their spring bias. When the compression body 144 is operating in this fashion, the first and second fingers 142 grip the superior endplate component between oppositely directed sides of the superior endplate component. When the compression body 144 is moved back towards the superior support 112, the compression body no longer bears against the shoulders defined by the first and second fingers 142 to allow the first and second fingers to move apart under their spring bias and to thereby release their grip on the superior endplate component.

The compression mechanism further comprises a compression mechanism driving arrangement which is supported on the superior arm 116 for movement relative to the superior arm. The compression mechanism driving arrangement comprises a first driving member 146 and a second driving member 148 which are hingedly coupled to each other by a first compression mechanism hinge 150. The first driving member 146 is coupled at its proximal end to the superior support 112 and is hingedly coupled at its distal end to a proximal end of the second driving member 148. The second driving member 148 is attached to the compression body 144 whereby the compression body moves with the second driving member 148. Movement of the first driving member 146 causes the second driving member 148 to move back and forth along the superior arm 116 whereby the compression body 144 moves between a first and second finger 142 compressing position and a first and second finger releasing position. The first driving member 146 is moved by way of a lever 152 which is rotatably mounted on the superior support 112. The lever 152 defines a cam profile that is operative to lock the position of the first driving member 146 and hence the position of the second driving member 148 when the second driving member is at its greatest reach. The lock thus provided by the lever 152 therefore locks the grip exerted on the superior endplate component by the first and second fingers 142. The first driving member 146 is structured to allow it to flex slightly when the lever 152 is moved to reduce likelihood of jamming of the compression mechanism driving arrangement.

Figure 5C:
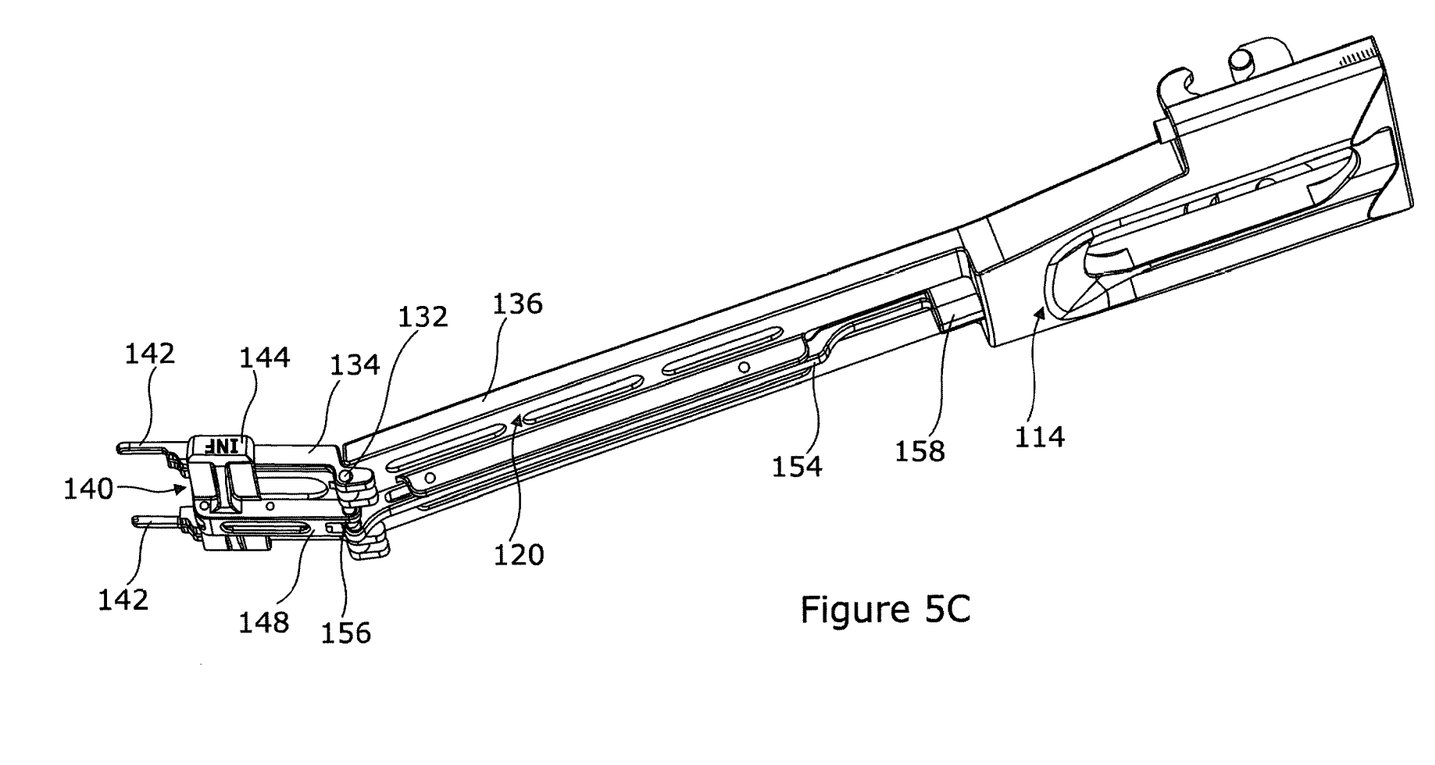
FIG. 5C is a view of an inferior part of the insertion instrument of FIG. 5A.

A view of an inferior part of the insertion instrument of FIG. 5A is shown in FIG. 5C. The inferior part comprises the previously described inferior support 114 and inferior arm 120, amongst other components. The inferior part further comprises an endplate gripping arrangement 140. Form and function of the endplate gripping arrangement 140 of the inferior part is common to the form and function of the endplate gripping arrangement 140 of the superior part except as will now be described. The reader's attention is directed to the previous description of the endplate gripping arrangement 140 of the superior part in respect of common form and function.

The compression mechanism driving arrangement of the inferior part comprises a first driving member 154 and a second driving member 148 which are hingedly coupled to each other by a second compression mechanism hinge 156. The first driving member 154 is coupled at its proximal end to the inferior support 114 and is hingedly coupled at its distal end to a proximal end of the second driving member 148. The second driving member 148 is attached to the compression body 144 whereby the compression body moves with the second driving member 148. Movement of the first driving member 154 causes the second driving member 148 to move back and forth along the inferior arm 120 whereby the compression body 144 moves between a first and second finger 142 compressing position and a first and second finger releasing position. The first driving member 154 is urged away from the inferior support 114 by a spring (not shown) mounted at the proximal end of the first driving member 154 which maintains by virtue of its spring bias the compression body 144 in the inferior endplate component gripping condition. A release button 158 at the proximal end of the first driving member 154 compresses the spring when the release button is pressed by a user. Compression of the spring releases the first driving member from the bias of the spring to in turn release the compression body 144 from its locked condition and thereby release the inferior endplate component from the grip exerted by the first and second fingers 142. The second compression mechanism hinge 156 differs from the first compression mechanism hinge 150 as will now be described. The distal end of the first driving member 154 defines a slot which extends generally in a direction of separation of the superior and inferior supports 112, 114. The hinge pin of the second compression mechanism hinge 156 is received in and travels along the slot in the distal end of the first driving member 154 to accommodate change in relative disposition of the proximal and distal portions 134, 136 of the inferior arm 120 as their extent of relative angulation changes. Furthermore, the axis of rotation of the second compression mechanism hinge 156 is slightly further away from the superior arm 116 than the axis of rotation of the hinge 132 between the proximal and distal portions of the inferior arm 120. Having the axis of rotation of the second compression mechanism hinge 156 offset in this fashion causes the compression mechanism driving arrangement to increase the extent of relative angulation of the inferior arm 120 and such that the distal portion 134 of the inferior arm is urged towards the superior arm 116.

The insertion instrument according to the second embodiment is formed from a standard surgical instrument metal, such as stainless steel. Alternatively, the insertion instrument according to the second embodiment is formed from a plastics material, such as polycarbonate or nylon. An insertion instrument formed from a plastics material is typically for single use before disposal.

The insertion instrument according to the second embodiment is used as described above with reference to the first embodiment with articulation of the inferior arm of the second embodiment providing the same benefits as articulation of the two inferior arms of the first embodiment.

The invention claimed is:

1. An insertion instrument for inserting a modular intervertebral fusion device or components thereof into an intervertebral space, the insertion instrument comprising:
   a superior arm mounted on a superior support such that the superior arm extends from the superior support; and
   an inferior arm mounted on an inferior support such that the inferior arm extends from the inferior support, wherein
   the superior and inferior supports are mechanically coupled to each other whereby: the superior and inferior arms extend in generally a same direction such that, in use, the distal end of each of the superior and inferior arms engages at a respective location on a modular intervertebral fusion device or component thereof; and the superior and inferior supports rotate relative to each other to provide relative rotation of the superior and inferior arms, whereby there is movement together and apart of the superior and inferior arms at their distal ends, and
   one of the superior and inferior arms is an unarticulated arm which is unarticulated between its distal end and the respective one of the superior and inferior supports, and wherein the other one of the superior and inferior arms is an articulated arm which is articulated between its distal end and the respective one of the superior and inferior supports,
   the articulated arm comprises a proximal portion, a distal portion and a hinge, the proximal portion extending from the respective one of the superior and inferior supports, the hinge rotatably coupling the proximal and distal portions to each other, and the distal portion extending from the hinge to the distal end of the articulated arm whereby the distal end of the articulated arm rotates towards or away from the distal end of the unarticulated arm,
   the unarticulated arm is immovably mounted on the respective one of the superior and inferior supports, and
   the proximal portion of the articulated arm is immovably mounted on the respective one of the superior and inferior supports.

2. The insertion instrument according to claim 1, wherein the unarticulated arm is substantially straight between its distal end and the respective one of the superior and inferior supports, and each of the proximal and distal portions is substantially straight.

3. The insertion instrument according to claim 1, wherein the hinge is between 20 mm and 100 mm from the distal end of the articulated arm.

4. The insertion instrument according to claim 3, wherein the hinge is between 50 mm and 70 mm from the distal end of the articulated arm.

5. The insertion instrument according to claim 1 comprising a pair of superior arms and a pair of inferior arms, the pair of superior arms mounted on the superior support such that the superior arms are spaced apart and extend generally parallel with each other from the superior support, the pair of inferior arms mounted on the inferior support such that the inferior arms are spaced apart and extend generally parallel with each other from the inferior support.

6. The insertion instrument according to claim 1, wherein the superior support and the inferior support rotate relative to each other about a support axis which is substantially orthogonal to a longitudinal axis of the arms and substantially orthogonal to a direction of separation of the superior and inferior supports.

7. The insertion instrument according to claim 6, wherein the superior support and the inferior support are mechanically coupled to each other to present a barrier to movement of the superior support and the inferior support relative to each other in a transverse direction.

8. The insertion instrument according to claim 1, wherein the superior support and the inferior support are mechanically coupled to each other: to allow the superior support and the inferior support to be moved together and apart; and to substantially prevent movement of the superior support and the inferior support relative to each other in a longitudinal direction.

9. An insertion instrument for inserting a modular intervertebral fusion device or components thereof into an intervertebral space, the insertion instrument comprising:
at least one superior arm mounted on a superior support such that the at least one superior arm extends from the superior support; and
at least one inferior arm mounted on an inferior support such that the at least one inferior arm extends from the inferior support, wherein
the superior support and the inferior support are mechanically coupled to each other whereby: the at least one superior arm and the at least one inferior arm extend in generally a same direction such that, in use, each of the distal ends of the superior and inferior arms engage at a respective location on a modular intervertebral fusion device or component thereof; and the superior and inferior supports rotate relative to each other to provide relative rotation of: the at least one superior arm; and the at least one inferior arm, whereby there is movement together and apart of the at least one superior arm and the at least one inferior arm at their distal ends,
one of: the at least one superior arm; and the at least one inferior arm is unarticulated between its distal end and the respective one of the superior support and the inferior support, and wherein the other one of: the at least one superior arm; and the at least one inferior arm comprises a hinge between its distal end and the respective one of the superior support and the inferior support, the hinge rotating the distal end of the other one of the superior arm and the inferior arm towards or away from the one of the superior arm and the inferior arm
the superior support and the inferior support are mechanically coupled to each other: to allow the superior support and the inferior support to be moved together and apart; and to substantially prevent movement of the superior support and the inferior support relative to each other in a longitudinal direction, and the superior support and the inferior support define inter-engaging profiles which cooperate to provide: for rotation of the superior support and the inferior support relative to each other; and for movement of the superior support and the inferior support together and apart, and wherein the inter-engaging profiles comprise a protrusion extending from one of the superior and inferior supports and a channel defined in the other of the superior and inferior supports, the protrusion being received in the channel, the channel extending in a direction of separation of the superior and inferior supports whereby the superior and inferior supports are rotatable relative to each other, and the superior and inferior supports are movable together and apart.

10. The insertion instrument according to claim 9, wherein a first set of inter-engaging profiles is on a first side of the superior and inferior supports and a second set of inter-engaging profiles is on a second side of the superior and inferior supports, the first and second sides facing in opposite directions.

11. The insertion instrument according to claim 1, wherein the superior support and the inferior support are mechanically coupled to each other: to substantially prevent movement of the superior support and the inferior support relative to each other in a direction of separation of the superior and inferior supports; and for movement of the superior and inferior supports relative to each other in a longitudinal direction.

12. The insertion instrument according to claim 11, wherein the inferior support comprises a spring bias which drives the superior support relative to the inferior support in the longitudinal direction such that the distal end of the at least one superior arm is driven further away from the inferior support.

13. The insertion instrument according to claim 5, wherein each of the pair of superior arms and each of the pair of inferior arms is mounted at its proximal end on a respective one of the superior and inferior supports, the arm mounted such that the arm is substantially immovable relative to its respective superior or inferior support with exception of rotation of the arm relative to the respective superior or inferior support and about the longitudinal axis of the arm.

14. The insertion instrument according to claim 13, wherein the distal end of each arm is shaped to be snugly and removably received in a recess defined in the intervertebral device or component thereof, and wherein the distal end of the arm and the recess define cooperating profiles which allow for insertion of the distal end of the arm into the recess and which present resistance to withdrawal of the distal end of the arm from the recess after the arm has been rotated relative to its respective superior or inferior support and about the longitudinal axis of the arm.

15. The insertion instrument according to claim 1 comprising only one superior arm and only one inferior arm.

16. The insertion instrument according to claim 15 comprising a gripping arrangement for each of the superior arm and the inferior arm, each gripping arrangement comprising first and second sprung fingers which extend from a distal end of the respective arm, the first and second sprung fingers spaced apart to sufficient extent to receive therebetween an endplate component of the intervertebral fusion device.

17. The insertion instrument according to claim 16, wherein each gripping arrangement further comprises a compression mechanism which releasably engages with the first and second fingers to compress the first and second fingers together towards their distal ends and against the spring bias, the endplate component being gripped by the first and second fingers when the compression mechanism has engaged with the first and second fingers.

18. The insertion instrument according to claim 17, wherein the compression mechanism comprises a compression body which is movably attached to its respective arm, the compression body mounted on the arm for movement along the arm, movement of the compression body along the arm providing for compression and release from compression of the first and second fingers.

19. The insertion instrument according to claim 17, wherein each gripping arrangement comprises a compression mechanism driving arrangement which is supported on its respective arm for movement relative to the arm, the compression mechanism driving arrangement comprising a first driving member and a second driving member which are hingedly coupled to each other, the first driving member coupled at its proximal end to the respective one of the superior support and the inferior support and hingedly coupled at its distal end to a proximal end of the second driving member, the second driving member attached to the compression mechanism whereby the compression mechanism moves with the second driving member.

20. An intervertebral device insertion assembly comprising an insertion instrument according to claim 1 and an intervertebral device or components thereof, the intervertebral device configured for engagement of each of the superior and inferior arms at respective spaced apart locations on the intervertebral device or on components thereof.

* * * * *